United States Patent [19]

Maklae et al.

[11] Patent Number: 5,081,352
[45] Date of Patent: Jan. 14, 1992

[54] TECHNIQUE FOR THE ANALYSIS OF INSULATING MATERIALS BY GLOW DISCHARGE MASS SPECTROMETRY

[75] Inventors: Gregory P. Maklae, Waltham; Daniel W. Oblas, Bedford; Donald L. Dugger, Marlboro, all of Mass.

[73] Assignee: GTE Laboratories Incorporated, Waltham, Mass.

[21] Appl. No.: 655,887

[22] Filed: Feb. 14, 1991

[51] Int. Cl.$^5$ .............................................. H01J 49/04
[52] U.S. Cl. .................................. 250/282; 250/288; 250/304
[58] Field of Search ........................ 250/282, 288, 304

[56] References Cited

U.S. PATENT DOCUMENTS 4,912,324  3/1990  Clark et al. ..................... 250/288
5,006,706  4/1991  Marcus ............................ 250/288

Primary Examiner—Jack I. Berman
Attorney, Agent, or Firm—Carl F. Ruoff

[57] ABSTRACT

The present invention describes a technique for sample preparation and analysis of ceramics and oxides. The technique involves mixing the ceramic or oxide powder with a conducting powder such as gallium, indium or silver and adding a small amount of dopant. The dopant comprises approximately 5–30% by weight of the sample and is selected from the group comprising thoria, yttria or ytterbia. It is theorized that the addition of the dopant provides a source of electrons that stabilizes the plasma in the glow discharge mass spectrometer which allows for impurity analysis in the part-per-million range.

7 Claims, 1 Drawing Sheet

TECHNIQUE FOR THE ANALYSIS OF INSULATING MATERIALS BY GLOW DISCHARGE MASS SPECTROMETRY

BACKGROUND OF THE INVENTION

The present invention discloses a method for analyzing ceramic materials to determine their impurity content. More specifically the present invention describes a Glow Discharge Mass Spectrometry (GDMS) analysis technique for determining trace impurity content in ceramic and ceramic-type materials such as alumina and silica.

Ceramic materials play an increasing role in meeting the needs of industry and society. Because of their high melting temperatures, thermal shock capabilities and resistance to harsh atmospheres, various ceramic products have found their way into such areas as automotive, lighting and space technologies. In order to minimize the chances of a part failing prematurely, the starting powders should be screened for contaminants, which may cause microscopic fracturing during forming operations or from mechanical stress during use. This quality control may be performed by various methods including spark source mass spectrometry, (SSMS), emission spectrography, inductively coupled plasma, spectrometry (ICP) or glow discharge mass spectrometry, (GDMS).

While emission spectrography does offer adequate sensitivity, it lacks accuracy, is time consuming and the photoplate may be difficult to interpret. SSMS offers similar sensitivity and better accuracy, but it lacks the resolution necessary to separate interference peaks from the peaks of interest. For example, the identification of the silicon dimmers from the iron and nickel peaks are not readily determined using SSMS because of isotopic interferences. Also, matrix effects of this technique can be severe, making it more standard dependent than GDMS. ICP offers good sensitivity and excellent accuracy, but sample preparation is difficult and time consuming for many ceramic materials, and great care must be taken not to volatilize any elements such as boron or silicon during the dissolution process with hydrofluoric acid.

In GDMS, the sample to be analyzed forms the cathode in a low pressure gas discharge. Argon is typically used as the gas. Positive gas ions are accelerated towards the cathode with energies of a few hundred electron volts thereby sputtering the sample. The sputtered neutral species diffuse through the discharge gas where some are ionized. The positive ions are extracted through a small slit and accelerated into a high resolution mass spectrometer for analysis.

The glow discharge produces a stable ion beam with few multicharged species and is therefore suited to producing consistent data. In contrast, the traditional spark ion source has poor ion stability and produces complex mass spectra which requires long integration times to optimize the sensitivity, commonly uses photographic plates for detection, as well as the need for a skilled operator to interpret the mass spectra on the photo plates.

While recently gaining in prominence, GDMS is an old analytical technique. Also, it is not the panacea for all elements. For example, potassium and calcium determinations at the low ppm range are not possible because of interferences from argon ions. Using a different discharge gas, such as xenon, reduces this problem, but at the expense of sensitivity. GDMS does offer excellent resolution (4000-10000 Daltons), straight forward sample preparation, and short analysis time.

Samples that are analyzed by GDMS must be conducting since they serve as one of the electrodes of a small hollow cathode cell. Therefore nonconducting material, such as insulating and ceramic materials must be mixed with a high purity conducting powder such as In(indium), Ga(gallium), or Ag(silver). For most insulating materials this procedure is quite satisfactory. However, it has been shown that materials such as silica and alumina cannot be run using the standard approach because the discharge (voltage and current) in the hollow cathode cell is not constant enough to allow for stable cell operation. This instability can be reduced if the sample to binder (silver, indium or gallium) ratio is reduced to 1 part Sample to 50 parts binder, or if the discharge parameters are extremely low, 0.2 mA. However, this stability is achieved at the expense of sensitivity, which now would be greater than 100 ppm for many elements.

The present invention describes a technique wherein ceramic materials that were previously not possible to analyze, such as alumina and silica, can be analyzed for impurities in the part-per-million range using GDMS.

SUMMARY OF THE INVENTION

The present invention describes a method for analyzing an oxide or ceramic sample for trace impurities. The method involves preparing the sample by mixing the oxide or ceramic material with a conducting powder such as gallium, indium or silver and a dopant such as yttria ($Y_2O_3$), thoria ($ThO_2$), or ytterbia ($Yb_2O_3$) to stabilize the discharge. The sample is then formed into a small rod suitable for analysis by glow discharge mass spectrometry. If the additive or dopant is not included in the mixture, the resulting cathode rod does not give a stable discharge and accurate analysis of impurities at the part-per-million level is not achievable.

DETAILED DESCRIPTION OF PREFERRED EMBODIMENTS

Figure 1:
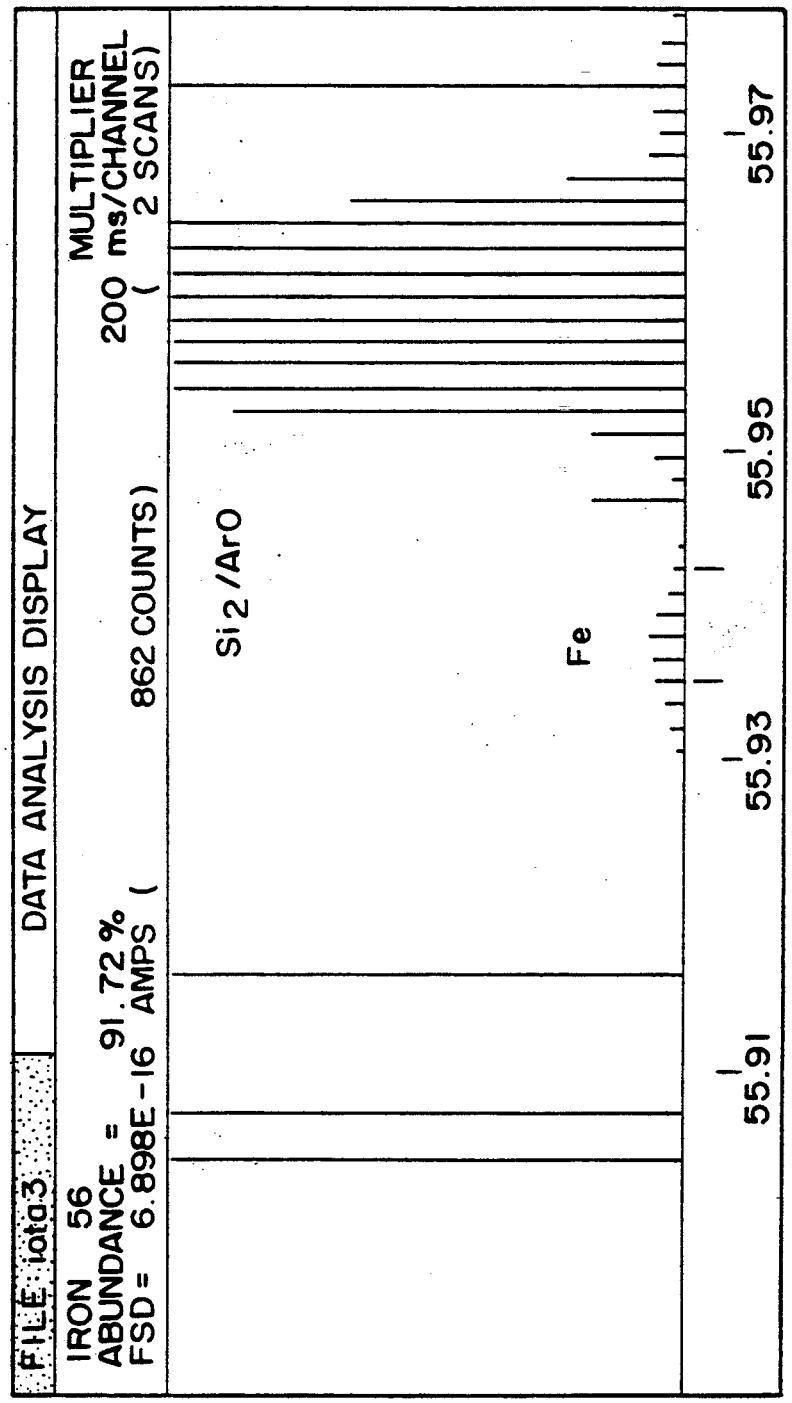
FIG. 1 shows that base line resolution of iron and nickel isotopes in a silicon matrix using GDMS.

The present invention describes a method of preparing nonconducting samples for GDMS. Nonconducting samples such as alumina and silica must be mixed with a conducting powder and a dopant additive to form a conducting electrode in order to produce a stable discharge. The method involves mixing powders of alumina or silica which are less than 37 microns with approximately 5-30% by weight of thoria ($ThO_2$), yttria ($Y_2O_3$) or ytterbia ($Yb_2O_3$) along with a conducting species such as indium, silver or gallium. The results of the analyzed samples indicate that improved plasma stability is obtained compared to mixing alumina or silica with only the conducting powders.

A VG9000 Glow Discharge Mass Spectrometer, equipped with a standard discharge cell was used for all of the following examples. The mass spectrometer is a double focusing, dual detector system with a maximum resolution of 10000 Daltons and a peak intensity dynamic range of $5 \times 10^7$ at 4000 Daltons, the typical operating resolution. This allows base line resolution of the major iron and nickel isotopes in a quartz matrix from $Si_2^+$ peak, a difference of 19 milli-mass units (FIG. 1). The standard cell is liquid nitrogen cooled to $-190°$ C. to minimize the contribution of water and CO in the discharge, which would have an adverse affect on its efficiency, and the stability of the discharge. The discharge gas is argon, which was obtained from liquid argon boil off and purified by passing it through a gettering furnace, Centorr model 2G-100-SS, prior to its introduction into the mass spectrometer.

EXAMPLE 1

Sample preparation for alumina, silica, silicon carbide and silicon nitride was as follows. Approximately 50 milligrams of sample powder were placed in a plastic vial with 300 mg of 37 micron 5N pure indium powder, which was obtained from Cerac Inc., Milwaukee Wisc., as well as two teflon balls 3/32" diameter. This was shaken for 5 minutes on a Spex 5100 Mixer/Mill to obtain a uniform blend. The sample-indium mix was loaded into a polypropylene plug that has a 2 mm $\times$ 18 mm hole drilled perpendicular in its cyclindrical axis, and pressed at 20000 pound for one minute to form the sample electrode. The sample was mounted into the mass spectrometer and a discharge was struck. The plasma was allowed to stabilize for thirty minutes before data collection commenced.

Samples of alumina and silica prepared in this manner would not discharge in a stable manner. The glow discharge power supply fluctuated over several hundred volts, and the accelerating voltage showed variations of 2 kV or more. Because of the nature of the sample (an insulator), it was theorized that a source of more freely liberated electrons was needed to sustain the discharge. It was found that the addition, several percent of yttria, silica, thoria or ytterbia to alumina; or yttria or thoria to silica would satisfy this need. Table I summarizes the composition of the optimum mixtures. It is also critical that the particle size of the alumina and silica powders be on the order of less than 50 microns. Therefore, these samples were passed through a 37 micron nylon sieve prior to the addition of indium, mixing and compacting.

TABLE I

| Matrix | Ceramic-Dopant Mixes | | mg Indium |
|---|---|---|---|
| | mg Matrix | mg Dopant | |
| Alumina | 65 | 20 $Y_2O_3$ | 330 |
| Alumina | 50 | 10 $Yb_2O_3$ | 325 |
| Alumina | 35 | 5 $SiO_2$ | 330 |
| Alumina | 50 | 15 $ThO_2$ | 325 |
| Silica | 52 | 16 $Y_2O_3$ | 300 |

Because the concentrations of silicon and yttrium were of interest in the alumina samples, the majority of the analyses involved the use of thoria as the additive to the electrode mixture to sustain the discharge.

The operating parameters of the discharge were also sample dependent, therefore, the optimum signal to noise ratio had to be determined for each sample type. Most oxide-nitride/indium mixtures could be analyzed with a discharge current of 1.5 mA and a discharge voltage of 800-900 volts without any significant breakdown. Alumina and silica on the other hand could only withstand a discharge voltage of 500-600 volts at a current of 1.5 mA. These parameters yielded a matrix signal of $2 \times 10^{-12}$ to $1 \times 10^{-11}$ amps for the alumina or silica samples, and greater than or equal to $1 \times 10^{-11}$ amps for most other oxides-nitrides while maintaining a background signal of less than $1 \times 10^{-17}$ amps. To minimize the chance that a stray arc would distort a peak beyond what is software correctable, the Daly counting time for the alumina and silica experiments was 200 milliseconds with each peak scanned once. For all other samples, the Daly counting time was set to 200 milliseconds, and two or three scans were taken of each peak. For all experiments, the Faraday counting time was 160 milliseconds, with 2 scans recorded for the major peaks.

RESULTS

For silica, the data were corrected for sensitivity variations by entering the standard VG sensitivity factors. These are based on the fact that the ion yield of all elements are within a factor of three of iron as discussed in the article by Guidobini et al., Journal of Crystal Growth 89, 1988. The results were accurate to approximately 50% for most samples, and no worse than a factor of two for any certified impurity when corrected using relative sensitivity factors (RSF's) based on NBS SRM 102 (a silica powder) and illustrated in Table II. Results are listed in ppm by weight.

TABLE II

| SRM 102 Silica Using $Y_2O_3$ Additive | | |
|---|---|---|
| Element | Cert. PPM | Calc. PPM |
| Al | 10400 | 20200 |
| Fe | 4620 | 4000 |
| Ti | 960 | 680 |
| Zr | 150 | 240 |
| P | 110 | 83 |
| Mn | 38 | 30 |
| Ca | 16400 | 15000 |
| Mg | 1260 | 1400 |
| K | 2410 | 2500 |

Detection limits of 1 ppm are attainable in high purity quartz as shown in Table III.

TABLE III

| Quartz Powder Using $ThO_2$ Additive | |
|---|---|
| Element | PPM |
| Na | 4.2 |
| Al | 18 |
| Ti | 0.93 |
| Fe | 5.5 |
| Mg | 1.1 |
| P | 0.91 |
| Cr | 0.54 |
| Ni | 2.0 |

Base line resolution is easily achieved between $^{56}Fe^+$ and $^{28}Si_2^+$, as demonstrated in FIG. 1.

Because of a great interest in developing a rapid and accurate method of alumina assaying at this laboratory, a set of sensitivity factors based on SRM 699 and BCS 394 (a British standard designation) alumina standards were developed. These improved the accuracy of the results from a factor of two, to less than 50%, (Table V). A list of these factors is outlined in Table IV.

TABLE IV

| Alumina Relative Sensitivity Factors (RFS) | |
|---|---|
| Element | Factor |
| Al | 1.00 |
| Na | 0.51 |
| Mg | 0.62 |
| Si | 0.99 |
| P | 1.94 |
| Ca | 0.33 |
| Ti | 0.26 |
| Fe | 0.67 |

TABLE IV-continued

| Alumina Relative Sensitivity Factors (RFS) | |
|---|---|
| Element | Factor |
| Zn | 2.80 |

TABLE V

| | Standard vs Calculated RSF's SRM 699 | | |
|---|---|---|---|
| | Without | PPM | | |
| Element | RSF'S | Standard RSF | Calculated | Cert. |
| Na | 8600 | 12000 | 4400 | 4377 |
| Mg | 5.7 | 6.5 | 3.5 | 3.6 |
| Si | 120 | 180 | 120 | 65 |
| Ca | 530 | 250 | 180 | 257 |
| Cr | 2.6 | 3.5 | 2.6 | 1.4 |
| Mn | 3.1 | 3.0 | 3.1 | 3.9 |
| Fe | 69 | 47 | 46 | 91 |
| Zn | 21 | 76 | 60 | 100 |

As with silica, the detection limits of alumina samples were in the ppm range, with an aluminum signal of $1 \times 10^{-11}$ amps achieved, (Table VI).

TABLE VI

| Polycrystaline Alumina Powder | | | |
|---|---|---|---|
| Element | PPM | Element | PPM |
| Na | 19 | Mg | 200 |
| Si | 480 | P | 1.8 |
| Cl | 65 | Ti | 9.1 |
| Cr | 5.2 | Mn | 1.8 |
| Fe | 23 | Ni | 3.0 |

From the experiments and results outlined above, it is apparent that glow discharge mass spectrometry can be used to analyze the impurity content of oxides and ceramics. Detection limits approaching 1 ppm are readily obtained. Sample preparation and analysis time are two hours per sample for up to 15 impurities. This is achieved with accuracy, sensitivity and precision that i lacing in other techniques such as SSMS or emission spectrography.

As shown in the above samples, thoria can be used to replace yttria as an additive to analyze ceramic materials under GDMS. The above examples show that less thoria than yttria is required to facilitate the running of silica and alumina. Typically 5-30% of weight of thoria is sufficient to produce a stable discharge. Polycrystalline alumina arc tubes often contain a minor amount of yttria as a sintering aid. Therefore the use of thoria allows the determination of the concentration of yttria in the alumina. This would not be possible if yttria was used as an additive to create a stable discharge. Another advantage of using thoria is that thorium has a higher atomic mass and therefore results in fewer interferences in the mass spectrum which allows for lower detection limits and easier data interpretation.

While the present invention has been shown and described what is at present considered the preferred embodiment of the invention, various changes and modifications will be obvious to those skilled in the art. All such modifications are intended to fall within the scope of the invention as defined by the appended claims.

What is claimed is:

1. A method for analyzing an oxide or ceramic sample for impurity content using Glow Discharge Mass Spectrometry comprising:
   mixing the oxide or ceramic sample with a conducting powder and a dopant selected from the group comprising yttria, thoria and ytterbia to form a homogenous mixture;
   forming the homogenous mixture into an electrode;
   analyzing the electrode for impurity content using a Glow Discharge Mass Spectrometer.

2. The method according to claim 1 wherein the oxide or ceramic is selected from the group consisting of alumina and silica.

3. The method according to claim 1 wherein the conducting powder is selected from the group consisting of indium, gallium, and silver.

4. A method for preparing an oxide or ceramic sample for Glow Discharge Mass Spectrometry comprising:
   mixing the oxide sample with a conducting powder and a dopant selected from the group comprising, yttria, thoria and ytterbia to form a homogenous mixture;
   forming the homogeneous mixture into a cathode rod suitable for mass spectrometric analysis.

5. The method according to claim 4 wherein the oxide or ceramic is selected from the group consisting of alumina, silica.

6. The method according to claim 5 wherein the weight percent of the dopant is approximately 5-30% of the weight of oxide or ceramic sample.

7. The method according to claim 4 wherein the conducting powder is selected from the group consisting of indium, silver, and gallium.

* * * * *